(12) United States Patent
DiFoggio et al.

(10) Patent No.: US 8,023,690 B2
(45) Date of Patent: Sep. 20, 2011

(54) APPARATUS AND METHOD FOR IMAGING FLUIDS DOWNHOLE

(75) Inventors: Rocco DiFoggio, Houston, TX (US); Raman Viswanathan, Houston, TX (US); Jeffery W. Fontenot, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 1131 days.

(21) Appl. No.: 11/669,616

(22) Filed: Jan. 31, 2007

(65) Prior Publication Data

US 2007/0120051 A1    May 31, 2007

Related U.S. Application Data

(63) Continuation-in-part of application No. 11/051,388, filed on Feb. 4, 2005, now Pat. No. 7,423,258.

(51) Int. Cl.
*G06K 9/00* (2006.01)

(52) U.S. Cl. ........................................ 382/100; 382/321

(58) Field of Classification Search .................. 382/100, 382/321; 175/40; 356/319, 325; 250/269.1; 399/159; 73/152.17, 152.25
See application file for complete search history.

(56) References Cited

U.S. PATENT DOCUMENTS

| | | |
|---|---|---|
| 4,774,573 A | 9/1988 | Mount, II et al. |
| 4,837,753 A | 6/1989 | Morris et al. |
| 4,901,069 A | 2/1990 | Veneruso |
| 4,994,671 A | 2/1991 | Safinya et al. |
| 5,204,527 A | 4/1993 | Buchanan ................ 250/390.07 |
| 5,859,430 A | 1/1999 | Mullins et al. |
| 6,176,323 B1 * | 1/2001 | Weirich et al. .................. 175/40 |
| 6,229,453 B1 | 5/2001 | Gardner et al. |
| 6,355,928 B1 | 3/2002 | Skinner et al. |
| 6,437,326 B1 | 8/2002 | Yamate et al. |
| 6,472,660 B1 | 10/2002 | Hother |
| 6,491,095 B2 | 12/2002 | Kompanek ..................... 166/249 |
| 6,627,873 B2 | 9/2003 | Tchakarov et al. ........... 250/256 |
| 6,859,032 B2 | 2/2005 | Heaton et al. ................. 324/303 |
| 6,874,361 B1 | 4/2005 | Meltz et al. ................ 73/152.32 |
| 7,016,026 B2 | 3/2006 | DiFoggio et al. |
| 7,030,806 B2 | 4/2006 | Fullerton ...................... 342/104 |
| 7,075,062 B2 * | 7/2006 | Chen et al. ................. 250/269.1 |
| 7,095,012 B2 | 8/2006 | Fujisawa et al. |
| 2003/0062472 A1 | 4/2003 | Mullins et al. |
| 2003/0106993 A1 | 6/2003 | Chen et al. |
| 2003/0223620 A1 | 12/2003 | Anxionnaz et al. |
| 2004/0069942 A1 | 4/2004 | Fujisawa et al. |
| 2004/0129874 A1 | 7/2004 | Torgersen et al. |
| 2004/0164237 A1 | 8/2004 | Jones et al. |
| 2004/0178336 A1 | 9/2004 | DiFoggio |
| 2004/0211894 A1 | 10/2004 | Hother et al. |
| 2004/0216521 A1 | 11/2004 | Shammai et al. |
| 2004/0252748 A1 | 12/2004 | Gleitman ...................... 374/130 |

(Continued)

OTHER PUBLICATIONS

Hawkeye Pulsable Infrared Emitters, IR-50 Series, www.hawkeyetechnologies.com.

(Continued)

*Primary Examiner* — Anh Hong Do
(74) *Attorney, Agent, or Firm* — Cantor Colburn LLP

(57) ABSTRACT

The disclosure, in one aspect, provides a method for providing an image of a fluid that includes passing light through the fluid, detecting light passing through the fluid at at least one wavelength and producing signals corresponding to the detected light, and processing the signals to provide the image of the fluid.

18 Claims, 5 Drawing Sheets

U.S. PATENT DOCUMENTS

| | | |
|---|---|---|
| 2005/0012036 A1 | 1/2005 | Tubel et al. |
| 2005/0269499 A1 | 12/2005 | Jones et al. ............... 250/269.1 |
| 2006/0027742 A1 | 2/2006 | Srivastava et al. |
| 2006/0175547 A1 | 8/2006 | DiFoggio et al. |
| 2007/0108378 A1 | 5/2007 | Terabayashi et al. |

OTHER PUBLICATIONS

Spectrometry Modules, RS232 Read-out Module, IR Microsystems.

Tutorial, Optical Meters and Detectors, Newport, Photonics, pp. 169-173, 10 Figs.

Microray, IR Microsystems—Solutions for the Detection of Infrared Light Uncooled βray Detector Series, Oct. 2001, pp. 1-4.

Gentile et al.; *Calibration of a pyroelectric detector at 10.6 βm with the National Institute of Standards and Technology high-accuracy cryogenic radiometer*, Applied Optics, vol. 36, No. 16, Jun. 1, 1997, pp. 3614-3621, 2 Tables, 4 Figs.

\* cited by examiner

APPARATUS AND METHOD FOR IMAGING FLUIDS DOWNHOLE

CROSS REFERENCE TO RELATED APPLICATIONS

This patent application is a continuation-in-part of and claims priority from U.S. patent application Ser. No. 11/051,388, entitled, "Method and Apparatus for Analyzing a Downhole Fluid Using A Thermal Detector," filed on Feb. 4, 2005.

BACKGROUND OF THE DISCLOSURE

1. Field of the Disclosure

The disclosure herein relates to imaging fluids downhole.

2. Description of the Related Art

Oil wells (also referred to as wellbores or boreholes) are drilled into subsurface formations to produce hydrocarbons (oil and gas). A drilling fluid, also referred to as mud, is supplied under pressure to drill the wellbores. A majority of the wellbores are drilled under over-burdened or overpressure conditions, i.e., the pressure gradient in the wellbore due to the weight of the mud column is greater than the natural pressure gradient of the formation in which the wellbore is drilled. Because of the overpressure condition, the mud penetrates into the formation surrounding the wellbore to varying depths, thereby contaminating the natural fluid contained in the formation, which fluid also is referred to herein as the "connate formation fluid" or the "connate fluid."

To estimate or determine the type or the components of the fluid, including oil, gas and water, in a formation at a particular wellbore depth or to estimate the condition of the reservoir surrounding the wellbore at the particular depth, tools, referred to as the formation evaluation tools, are used during drilling of the wellbore and after the wellbore has been drilled to obtain samples of the connate fluid for analysis. After drilling the wellbore, such tools are conveyed via a wireline or coiled tubing. During drilling of the wellbore, such tools are disposed in a bottomhole assembly above the drill bit, which assembly is conveyed by a drill string that may include a coiled tubing or may be made up of jointed tubulars. To obtain a sample of the connate fluid, a probe is often used to withdraw the fluid from the formation. However, the formation fluid up to a certain distance adjacent the wellbore is contaminated with the mud (i.e., it includes the mud filtrate). Therefore, to obtain a clean sample of the formation fluid, the formation fluid withdrawn from the formation for an initial time period is discarded to ensure that the sample is a clean sample. Various sensors have been used to estimate when the fluid being drawn is clean or of an acceptable quality level, i.e., that the contamination level is acceptable. However, such methods do not provide a visual image of the fluid being withdrawn. Real time visual images can be helpful to an operator for taking samples. Therefore, there is a need for an apparatus and method for obtaining visual images of the fluid downhole.

SUMMARY OF THE DISCLOSURE

The disclosure herein, in one aspect, is a method that provides an image of a fluid: the method, in one aspect includes exposing the fluid to light, detecting light received from the fluid at a plurality of selected wavelengths, and processing signals corresponding to the detected light at the selected wavelengths to provide a visual image of the fluid. The image may include an image of interfaces between immiscible fluids or between solids, such as sand, and a fluid or between bubbles and a liquid. In another aspect, the method includes estimating darkness of the fluid from light detected at a plurality of selected wavelengths and providing a visual image of the fluid using the estimated darkness of the fluid at the selected wavelengths. In another aspect, the disclosure provides an apparatus for imaging a fluid that includes a light source that exposes the fluid to light, a detector that detects light received from the fluid at a plurality of wavelength and a processor that processes signals corresponding to the detected light to provide an image of the fluid. The detector, in one aspect, is a pyroelectric detector that is tuned to detect light at the selected plurality of the wavelengths. In one aspect, a hyperspectral imaging technique is used to produce the image of the fluid. The image may be a chemical specific image, which may include images corresponding to oil, gas and water, among other things.

BRIEF DESCRIPTION OF THE DRAWINGS

For detailed understanding of the disclosure, references should be made to the following detailed description of the drawings, taken in conjunction with the accompanying drawings, in which like elements in general have been given like numerals, wherein.

DETAILED DESCRIPTION OF THE DRAWINGS

The present disclosure, in one aspect, provides an apparatus for imaging a fluid downhole. In another aspect, the disclosure provides an apparatus for in-situ imaging of a fluid downhole that utilizes a broadband light source and a tunable thermal detector, such as an array of pyroelectric detectors. In another aspect, the disclosure provides a method of imaging a fluid downhole during withdrawal or extraction of the fluid from a formation.

Figure 1:
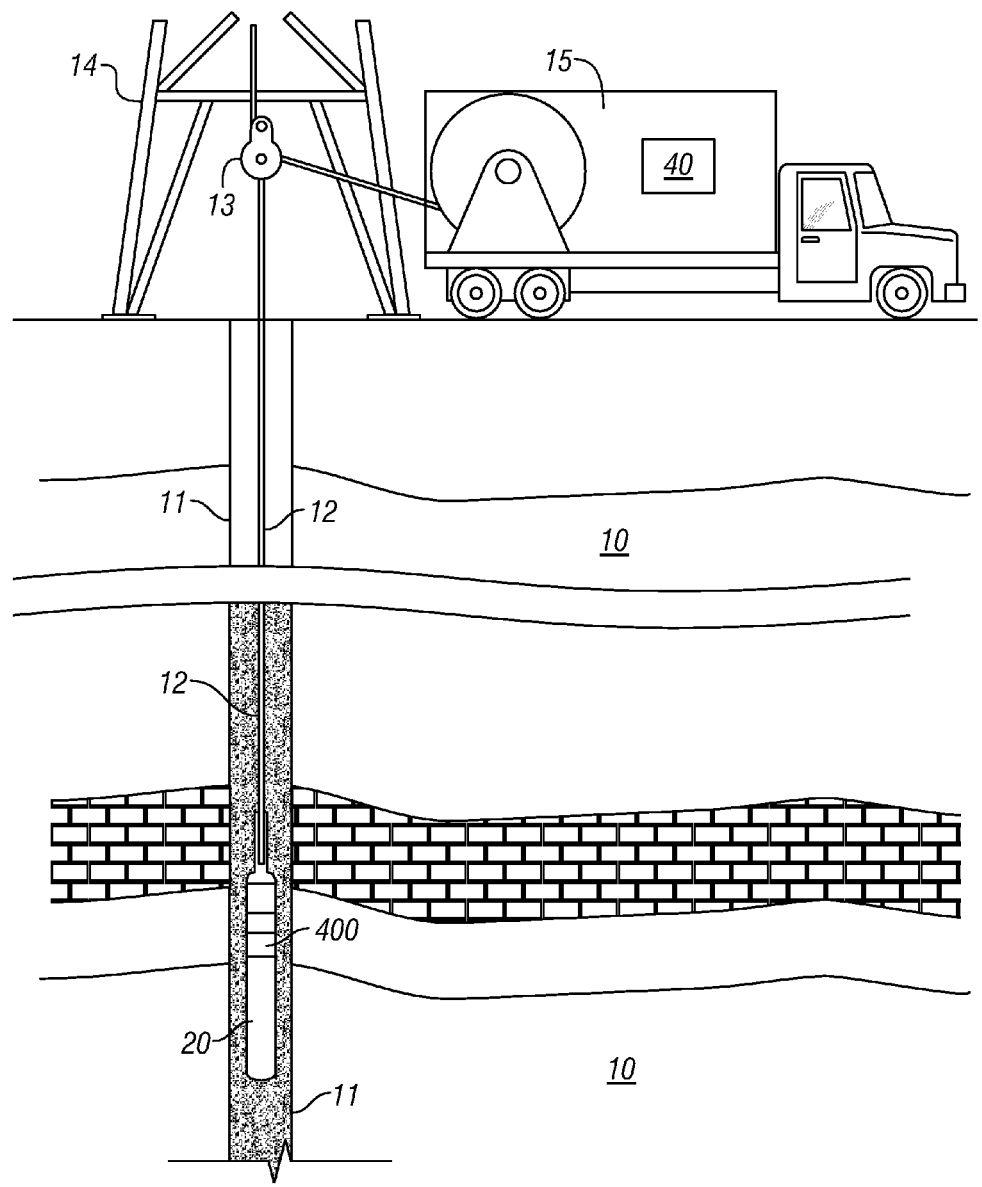
FIG. 1 is a schematic illustration of a tool made according to one embodiment of the disclosure conveyed into a wellbore for imaging a fluid obtained from the formation surrounding the tool.

FIG. 1 is a schematic representation of a cross-section of an earth's subsurface along the length of a wellbore 11 drilled in the formation 10. Usually the wellbore is at least partially filled with a mixture of liquids 16, which typically include water, drilling fluid (mud) and formation fluids indigenous to the earth formations, such as oil, gas and water. The fluid in the wellbore is referred to herein as the "wellbore fluid." The term "connate fluid" or "natural fluid" herein refers to the fluid that is naturally present in the formation, exclusive of any substantial contamination by fluids not naturally present in the formation, such as the mud, other chemical that may have been introduced into the wellbore or fluids that may have migrated from other formations or wells. Conveyed in the wellbore 11 at the bottom end of a wireline 12 is a formation evaluation or testing tool 20 that includes a subassembly or module 1 containing the imaging apparatus 400, according to one embodiment of the present disclosure, as described in more detail in reference to FIGS. 2-7. The wireline 12 typically is an armored cable that carries data and power conductors for providing power to the tool 20 and a two-way data communication (telemetry) between a tool processor 50 and a controller 40 at a surface unit 15. The wireline 12 typically is carried from the surface unit 15 over a pulley 13 supported by a derrick 14. The surface unit 15 may be a mobile unit for land operations and a fixed unit on an offshore rig or vessel for underwater operations. The surface controller 40 may include a computer or a microprocessor; data storage devices, such as solid state memory and magnetic tapes; peripherals, such as data input devices; display devices; and other circuitry for controlling and processing data received from the tool 20. The surface controller 40 also includes one or more computer programs embedded in a computer-readable medium accessible to the processor in the controller 40 for executing instructions contained in the computer programs to perform the various methods and functions associated with the operations of the tool 20, including, but not limited to, processing data from the tool 20 and providing images of the fluid.

Figures 2, 7:
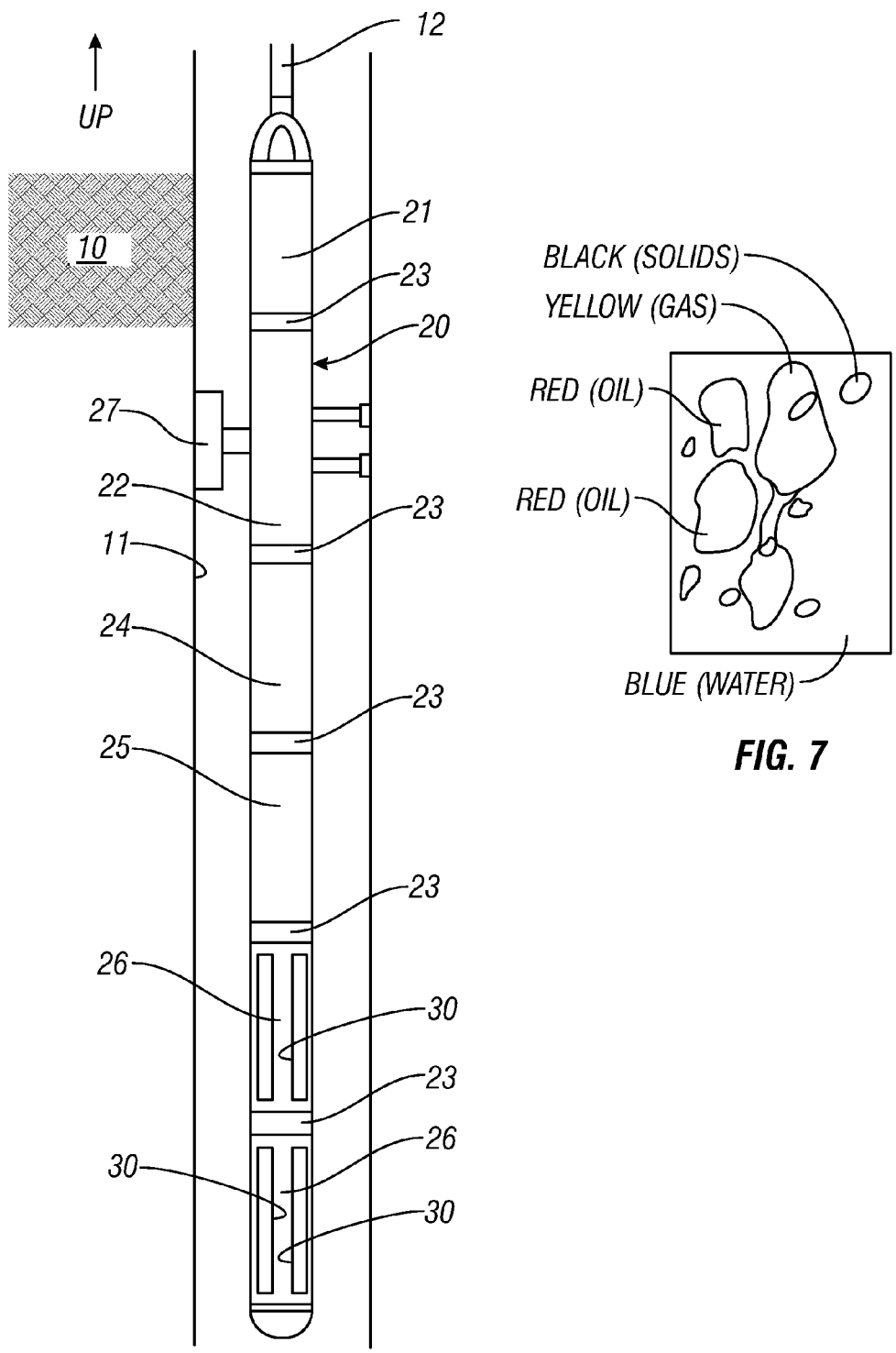
FIG. 2 is a schematic illustration of certain details of a portion of the tool of FIG. 1 placed at a selected location or depth in the wellbore for retrieving fluid from the formation and for providing in-situ visual images of the retrieved fluid.
FIG. 7 is an exemplary visual image of a fluid that may be provided by the imager made according to one embodiment of the disclosure.

FIG. 2 illustrates in more detail an embodiment of the formation evaluation or sampling tool 20 that includes an imaging apparatus 400 for providing images of the fluid being withdrawn from the formation 10. The sampling tool 20 is shown to be an assembly of several tool segments or modules that are mechanically joined end-to-end by a suitable mechanism 23, such as threaded joints or mutual compression unions. The tool 20 includes a power unit 21, (a hydraulic or electromechanical) segment and a formation fluid extractor 22 segment. Below (downhole) the extractor 22, a large displacement volume motor/pump unit 24 is provided for pumping fluid from the formation 10 into the wellbore 11 and/or one or more sample tanks or chambers 30. Below the large volume pump 24 is shown a similar motor/pump unit 25 having a smaller fluid displacement volume, which fluid may be imaged by the imaging apparatus. Ordinarily, one or more sample tank magazine sections 26 are assembled below the small volume pump 25. Each sample tank magazine section 26 may include one or more fluid sample tanks, such as tanks 30. The formation fluid extractor 22 comprises an extensible suction probe 27 that is opposed by wall feet 28. Both the suction probe 27 and the opposing feet 28 are extensible (hydraulically or electromechanically) to firmly engage the wellbore wall. A fluid extraction tool is described in U.S. Pat. No. 5,303,775, which is incorporated herein by reference.

The imaging apparatus 400 (also referred to herein as the imager) may provide continuous or substantially continuous images of the fluid as it is being withdrawn. In operation, the probe 27 and the feet 28 are extended so that the probe sealingly presses against the borehole wall. The pump 24 is used to pump the fluid from the formation into the tool 20 via the probe 27. A portion of the fluid is passed into or through a sample chamber (such as chamber 406, FIG. 4) associated with an imaging apparatus 400. The imager 400 detects light that passes through or reflected by (depending upon the configuration used) the fluid at one or more selected wavelengths and processes signals corresponding to the detected light to provide images of the fluid. The components or elements in the fluid detected by the imager 400 may include methane (which is a main component of natural gas), asphaltenes, oil, water, solids (such as sand) and known tracers added into a drilling fluid during drilling of the wellbore. The imager 400 alone or in combination with the surface controller 40 provides visual images of the fluid that may show the presence of the various elements in different colors or in different shades of grey. To reproduce a sample's visible colors, the imager may be configured to combine red, green, and blue monochrome images. To image chemical composition, the imager may be configured to combine various infrared monochrome images and use them to generate selected (or false) colored images, which represent particular chemical compounds. For example, a faded red may be used to indicate a lesser amount of gas compared to deep red, etc. The imager 400 may be configured to process the data or signals corresponding to the light detected at the various wavelengths and send to the surface controller 15 in-situ images of the fluid that may be displayed on a suitable display for visual presentation. Alternatively, the imager 400 may be configured to process signals to certain extent and transmit the processed signals to the surface processor 40 for further processing of such signals and for providing visual images of the fluid. The operation of the imager is explained in more detain in reference to FIGS. 4-6.

Figure 3:
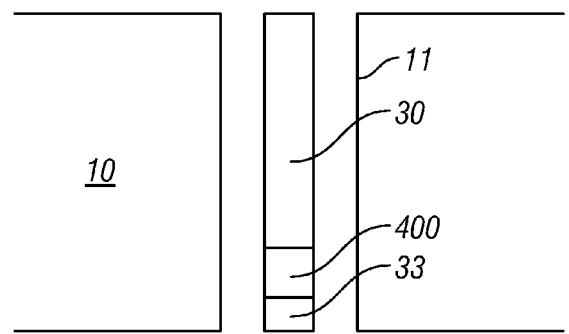
FIG. 3 is a schematic diagram showing the tool of FIG. 2 attached to a drill string that is conveyed in a wellbore for providing images of the fluid during drilling of the wellbore.

The imager 400 may be incorporated into a bottomhole assembly attached to a bottom end of drill string 30 above a drill bit 33 for providing images during drilling of the wellbore 11, such as shown in FIG. 3. In this configuration, the imager 400 provides images to a surface controller 40 or sends data relating to the images of the fluid via a suitable telemetry system, such as mud pulse telemetry, electromagnetic telemetry or an acoustic telemetry system.

Figure 4:
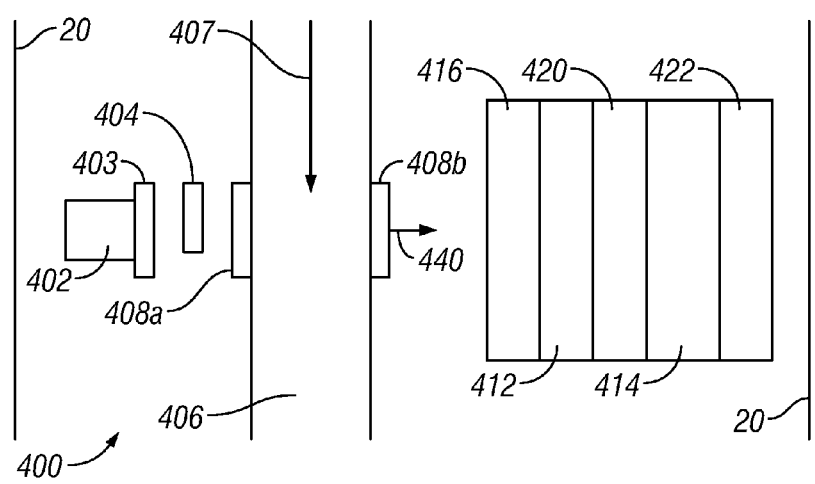
FIG. 4 is a schematic diagram of certain elements of an imaging device made according to one embodiment of the disclosure.

FIG. 4 is a schematic diagram showing a configuration of a portion of the imager 400 according to one exemplary embodiment. The imager 400 is shown to include a light source 402 that may be a broadband light source, such as a tungsten light source or any other light source that produces light within a desired or selected wavelength range, which light is used to illuminate the fluid. In one aspect, a light modulator 404 is provided. The modulator may be any suitable device that can vary the intensity of the light source, including, but not limited to, an electronic pulser that provides power to the light source, a mechanical chopper that interrupts the path of the light source to the downhole fluid, and an optical beam steering device. Thus, any suitable modulator may be used to modulate the light intensity that impinges on the fluid and the detector. A reflector or collimator 403 may be provided to focus and/or concentrate light from the light source 402 toward an optical window 408a of a fluid chamber 406. The optical window, in one aspect is a sapphire window. The fluid 407 extracted from the formation passes through the chamber 406. The various elements in the fluid, such as oil, gas, water, asphaltenes, solids etc., absorb the incident light received via the optical window 408a. The unabsorbed light passes through the fluid 407 and leaves the chamber or conduit 406 via an opposing window 408b.

The imager 400 further includes a detector 412 for detecting light that passes through the fluid 407. In one configuration, the detector 412 is a suitable thermal detector, which may be a pyroelectric detector array. Pyroelectric detectors respond to changes in the detector temperature and not to the ambient temperature. Therefore, they respond to changes in the intensities of any wavelength (color) of light that strikes them regardless of the ambient temperature. The detector 412, in one aspect, may be configured or tuned to detect (or view) any suitable wavelength or wavelengths, including, but not limited to, wavelengths sufficiently long to detect light beyond the asphaltene-absorbing region of crude oil, at which wavelengths crude oils tend to be translucent. The imager 400 utilizes a tunable filter 416 to create images of the fluid downhole at any desired wavelength of light, including infrared wavelengths, which can allow chemical imaging. In this manner, selective images of oil, water gas and other elements can be obtained. The imager 400 thus in one aspect utilizes suitable filter 416 interposed between the light 440 radiating from the fluid 407 and the detector 412. In one aspect the light source 407 provides broadband light and the filter 416 is tuned to sweep a selected range of wavelengths. Alternately, the filter 416 may sequentially allow selected wavelengths of light to pass to the detector 412. Thus, the detector 412 detects light at a number of selected wavelengths. In one aspect, the wavelength range may be from about 400 nm to about 2000 nm, which includes relevant wavelengths at which elements like water, methane at various temperatures and pressures, asphaltenes and various grades of oil absorb light. In another aspect, the detector may be tuned to a number of specific or particular wavelengths of light that are used by the imager 400 to provide images of the fluid or signals corresponding to the light detected at such wavelengths to the surface controllers 40 (FIG. 1), which processes such signals to provide the visual images.

In one aspect, the imager 400 includes a spectrometer 414 and processor 422 for analyzing the signals from the detector 412 and to provide images of the fluid. The detector 412 detects the intensity of light at the selected wavelengths or narrow bands (channels) of light, as described above, and provides signals corresponding to the detected light to the spectrometer 414. The light that is provided to the fluid is known. The absorbance of the light at each of the selected wavelength or narrow bands (channels) is determined. In other words the detector can provide signals that correspond to the observed darkness of the sample at these selected wavelengths or channels. A high gain amplifier 420 may be used to amplify the signals from the detector 412. The spectrometer 414 provides a spectrum of the light detected by the detector 412. The processor 422 utilizing the spectrum provides the images of the fluid. The processor 422 or the processor 40 at the surface may be configured to utilize a hyperspectral imaging technique to create visual images of the components of the fluid. A memory associated with the processor 422 contains computer programs, algorithms and data that are used by the processor 422 to provide the images of the fluid.

There are certain wavelengths at which most fluids absorb little or no light. Water absorbs very little light at 1300 nm and crude oils absorb very little light at either about 1300 nm or about 1600 nm. However, solids obstruct light at all wavelengths including 1300 nm and 1600 nm. Therefore, the processor may use the received light at or about either of these wavelengths, compare it with the induced light or an established baseline to estimate the size and location of the solids in the fluid and provide an image of the solids in the fluid. The processor also may be programmed to assign a color and a shade within the color based on the estimated quantity of the solid, such as the sand concentration. The detector may be made to contain an array of individual detectors so that they can provide the signals corresponding to corresponding areas of the window. The size of the individual detectors can define the spatial resolution of the image.

The peak absorbance for water at 25 degrees centigrade in the range of 400 nm to 2000 nm has been found to occur at wavelengths of about 1452 nm and 1933 nm. Water absorbance remains high over the wavelength range 1400 nm to 1525 nm and the range 1880 nm to 2100 nm. The detector may be tuned to detect light at or near such wavelengths and the processor 422 then may determine the absorbance at such wavelengths and utilize such information to provide images of water. Other wavelengths, such as 1420 nm and 1935 nm also have been found to provide adequate measurements of absorbance by water.

Absorbance of liquid oil is relatively high from about 1700 nm to 1775 nm with peaks occurring at around 1725 nm and 1765 nm, where the middle of the absorbing region is around 1740 nm. The processor 422 may be programmed to determine the absorbance of oil at selected wavelengths in the above noted range. The difference in absorbance at wavelengths of 1740 nm and 1600 nm may be used to estimate the fractional concentration of liquid hydrocarbon for various grades of crude oil by dividing this absorbance difference by the typical absorbance difference when the oil concentration is 100%. The subtraction of the absorbance at 1600 nm removes a portion or substantial portion of the baseline rise caused by the underlying tail of the asphaltene peak, which varies from one crude oil to another crude oil.

Asphaltenes, which are dark brown in color, absorb more light at wavelengths corresponding to violet light than they do at yellow light and even less at red light. Gas typically appears less absorbing than crude oil at 1740 nm both because it is less dense than a liquid hydrocarbon (so its concentration of carbon-hydrogen bonds is lower) and because its peak absorbance occurs at 1667 nm, which is on the left side of the liquid hydrocarbon peak.

Still referring to FIG. 4, the processor 422 may be programmed to determine the absorbance for asphaltene and gas in the same manner as described for oil and water at selected wavelengths. The processor 422, therefore, utilizing the absorbance (or intensity of light) at one or more selected wavelengths, provides an image of the downhole fluid. The processor 422 compares the absorbance values at certain wavelengths and utilizes data and/or algorithms that may be based on laboratory tests to estimate the amounts and location of the various elements present in the fluid and provide an image of the fluid. The processor 422 may send the relevant data to the processor 40 at the surface, which then may perform the above-noted functions to provide the images. The fluid images may be provided in-situ, i.e., while the fluid is being extracted from the formation.

In another aspect, one or more known chemicals or tracers may be introduced into the drilling fluid and the detector may be tuned to specific wavelengths at which such known tracers have high absorbance compared to the elements of the connate fluid. The imager may use such information to estimate the mud filtrate and provide a corresponding image.

In another aspect, the processor 422 or 40 may assign different colors to the different chemicals in the fluid, thereby providing a false-colored image in which color indicates the chemical being imaged. Alternatively, various shades of gray or intensities any single color may be used to provide the images.

The imager 400 may be configured to use any suitable method or circuitry to create images. For example, a control circuit for the imager 400 may cycle at a rapid speed to allow the generation of one-dimensional high resolution image, for example by using a high resolution array such as a linear 64-pixel pyroelectric array Arrays having any other resolution may also be used. The imager 400, using a moving mirror or another suitable scanner, can create a two-dimensional image from a series of such one-dimensional scans. Thus, in one aspect, a single detector and a two-dimensional scanning mirror may be used to create two-dimensional images. In another aspect an array of detectors tuned to scan selected wavelengths may be utilized. In another aspect, an acoustooptic tunable filter may be utilized to project only one color of light at a time and so create images at any wavelength of light, including infrared wavelengths, which can allow chemical imaging. In this manner, the scanner can selectively image elements, such as oil and water. With the pyroelectric array set up to view long wavelengths, one can see beyond the asphaltene peaks of crude oils, making them translucent.

Figure 5:
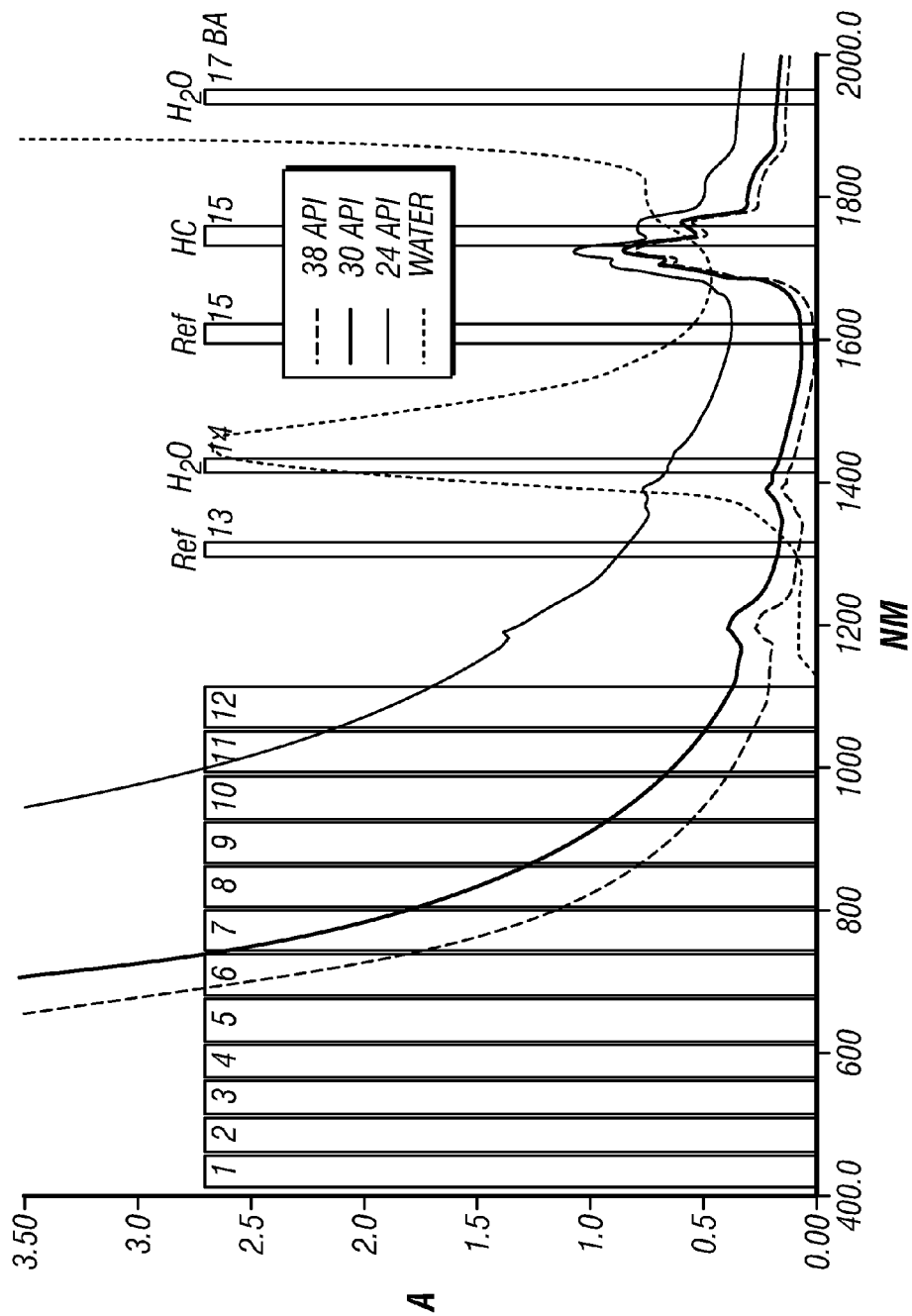
FIG. 5 shows absorbance spectra of certain crude oil grades and water.

FIG. 5 shows absorbance spectra 500 for three selected crude oil grades and water. The absorbance spectra 500 are provided herein to illustrate certain aspects of the method or process used by the imager to provide images of a downhole fluid. The graph of FIG. 5 shows absorbance (in a log scale) along the vertical axis and the wavelength of the detected light by the detector of the imager along the horizontal axis. The vertical bars shown refer to the channels that may be used by the imager for processing signals. The channel size (wavelength band) and the number of channels used are for illustration purposes only. Each channel, however, typically corresponds to a narrow wavelength band. As shown, absorbance for water has a peak around 1452 nm while the various crude oil grades have absorbances peaks at 1725 nm and 1760 nm, which can be monitored by a single channel at 1740 nm. The imager 400 determines absorbance for oil at one or more wavelengths in the wavelength band 1725 nm-1765 nm and for water around 1452 nm. The imager may determine the absorbance for solids at one or more wavelengths, such as around 1300 nm and/or 1600 nm where absorbance by the solids is substantially greater than the absorbance by either oil or gas. Thus, in essence, the imager 400 is configured to detect light at selected wavelengths where each such wavelength is highly absorbed by a particular chemical of interest and minimally absorbed by a another chemical of interest.

Figure 6:
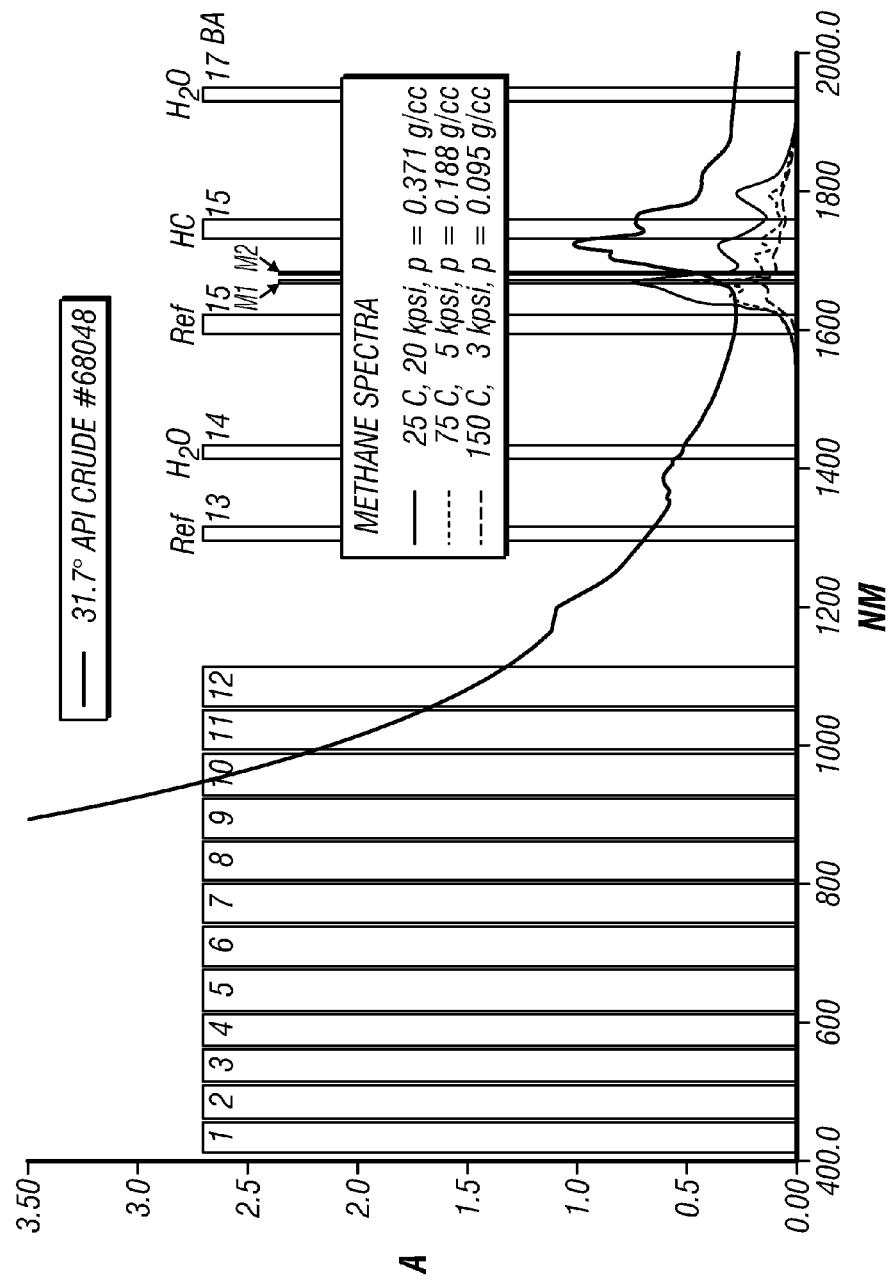
FIG. 6 shows absorbance spectra of methane at various pressures and temperatures compared to a laboratory spectrum of a particular crude oil.

FIG. 6 shows absorbance spectra for methane (gas) at various temperatures and pressures and an absorbance spectrum for a particular grade (31.7° API) of crude oil. Absorbance peak for natural gas, which is mostly methane, occurs around 1667 nm compared to oil, whose absorbance peak is centered around 1740 nm. The absorbance at 1740 nm for gas is lower than that of oil so, at that wavelength, gas typically appears as a weakly absorbing hydrocarbon. The imager 400 may be tuned to detect gas peaks and compare with the oil and water peaks to estimate the presence and amount of gas in the fluid.

Thus, as described above, the disclosure herein, in one aspect, provides an apparatus for imaging a fluid that includes a light source for illuminating a fluid downhole, a detector for detecting from the fluid at one or more selected wavelengths and provides signals corresponding to the detected light, a spectrometer that provides a spectrum of the detected light and a processor that utilizes the spectrum to provide images of the fluid. In one aspect, the light source is a broad band light source, such as a tungsten light source. Any other suitable light source may also be utilized. In one aspect, the detector is a thermal detector, such as a pyroelectric detector that may include a single detector or an array of detectors. A suitable tunable filter may be utilized to provide light to the detector at selected wavelengths within a selected range of wavelengths where the various elements or chemicals of interest in the downhole fluid absorb light.

The filter may be tuned to any suitable wavelength that may be one or more of: (i) a wavelength at which light is not substantially absorbed by natural oil present in a downhole formation; (ii) a wavelength at which light is not substantially absorbed by natural oil present in a formation and a wavelength at which light is absorbed by the natural oil present in the formation; (iii) about 1300 nm and 1600 nm; and (iv) a wavelength at which light is not substantially absorbed by a natural oil present in a formation downhole but is absorbed by water present in the formation. The apparatus further may include a spectrometer and a processor. The processor may utilize signals provided by the detector corresponding to at least two wavelengths to provide the image of the fluid.

The image provided by the processor may include images of oil, gas, water, known tracers added to the drilling fluid and solids present in the fluid. The apparatus may include a pump that extracts the fluid from the formation via a probe. In one aspect, a chamber or a flow line receives the extracted fluid. The chamber includes one or more optical windows, such as sapphire windows, for receiving light from the light source and for transmitting light after it has passed through the fluid. The detector is positioned to receive the light from the fluid. The spectrometer apparatus herein may provide absorbance of light at the wavelengths exposed to the detector. The processor may process the information from the spectrometer and additional information that may be stored for the processor to provide two-dimensional or three-dimensional images. The stored information may be laboratory data, baseline information, color assignments, etc. The imager may be conveyed into the wellbore via any suitable conveying member, including a wireline, slickline, coiled tubing and a drill string. Additionally, in any embodiment, the downhole processor 422, or the surface processor 40 or combination of the two may be configured to perform any of the aspects relating to the processing of detected signals to produce desired images.

FIG. 7 shows an example of an image of the fluid that may be produced by the imager 400. In this particular image the processor assigns color blue for water, red for oil, yellow for gas and black for solids. Any other color scheme may also be used. Also, different gray scales may be used to depict the images. Different shades of a same color may be used to show a measure of a particular component (such as volume). The image may be a two-dimensional image or a three-dimensional image. Referring to FIGS. 4 and 7, in practice, the system may produce images periodically or substantially continuously so that images of the fluid 407 flowing through channel 406 may be viewed in motion (video). The controller also may be programmed to estimate the percent of cleanup based on the amount and intensity of colors in the image.

In another aspect, a method is disclosed for providing an image of a fluid downhole that includes: illuminating the fluid downhole to light; detecting light from the fluid at a plurality of selected wavelengths of light by a detector that provides signals corresponding to the detected light; and processing the signals to provide a visual image of the fluid. The light source, in one aspect, is a broadband light source, such a tungsten light source. The method further may include tuning a filter to the selected wavelengths during withdrawal of the fluid from a formation downhole and processing the signals to provide the image in-situ. In the method, the processing may be done by a processor downhole and/or at the surface to provide an image that provides visual indication of one or more elements or chemicals of the fluid, including oil, water, methane, asphaltene, tracers added into the drilling fluid and solids. The fluid may be passed through a chamber and the light passing through the fluid may be detected continuously over a selected period of time to provide in-situ images of the fluid over the selected time period. Fluid contamination may be visually estimated or quantified by the imager.

Additionally, a computer-readable medium that is accessible to a processor for executing instructions contained in a computer program embedded in the computer-readable medium to provide image of downhole fluids is provided. In one aspect, the computer program includes: instructions to activate a light source for illuminating a fluid; instructions to tune a detector that is positioned to detect light from the fluid at a plurality of wavelengths; instructions to receive signals from the detector; and instructions to process the received signals to provide an image of the fluid. The computer program further may include instructions to compare absorbance at a plurality of wavelengths to provide the image of the fluid. The computer program may also include instructions to provide the image that shows the presence of one or more elements of the fluid, such as oil, methane, water, tracers and solids. Additionally, a system is disclosed for providing images of a fluid extracted from a formation, wherein the system includes a tool that is deployable into a wellbore by a conveying member from a surface location, wherein the tool includes: a pump for extracting the fluid from the formation; a chamber for receiving the extracted fluid; a light source that generates light that is exposed to the fluid in the chamber; a detector that receives light from the fluid in the chamber at a plurality of wavelengths and produces signals corresponding to the detected light; and a processor that utilizes the signals produced by the detector to provide an image of the fluid.

The foregoing disclosure is directed to the preferred embodiments of the disclosure various modifications will be apparent to those skilled in the art. It is intended that all variations within the scope of the appended claims be embraced by the foregoing disclosure. Examples of the more important features of the disclosure have been summarized rather broadly in order that the detailed description thereof that follows may be better understood, and in order that the contributions to the art may be appreciated. There are, of course, additional features of the disclosure that will be described hereinafter and which will form the subject of the claims appended hereto.

The invention claimed is:

1. An apparatus for imaging a fluid downhole, comprising:
    a light source for illuminating the fluid downhole;
    a pyroelectric detector that detects light from the fluid at a plurality of wavelengths and provides signals corresponding to the detected light; and
    a processor that processes the signals to determine an optical image of at least one of oil, gas and solid present in the fluid.

2. The apparatus of claim 1, wherein the light source is a broad band light source.

3. The apparatus of claim 1, wherein the plurality of wavelengths include at least one of: (i) a wavelength at which light is not substantially absorbed by natural oil present in a downhole formation; (ii) a wavelength at which light is not substantially absorbed by natural oil present in a formation and a wavelength at which light is substantially absorbed by the natural oil present in the formation; (iii) a wavelength at about 1300 nm and 1600 nm; (iv) a wavelength which light is not absorbed by natural oil present in a formation but is absorbed by water present in the formation; and (v) a plurality of wavelengths where at each such wavelength light is highly absorbed by one element of interest and relatively minimally absorbed by another element of interest.

4. The apparatus of claim 2 further comprising a filter for tuning the detector at the plurality of wavelengths.

5. The apparatus of claim 4, wherein the processor utilizes signals provided by the detector corresponding to each wavelength in the plurality of wavelengths to provide the image of the fluid.

6. The apparatus of any of the claim 1 further comprising a chamber that contains the fluid and includes at least one window for receiving the light from the light source for illuminating the fluid.

7. The apparatus of claim 6 further comprising a pump that pumps fluid from a formation into the chamber.

8. The apparatus of any of claim 7, wherein the processor is located at one of: (i) a surface location; and (ii) in a downhole tool.

9. A method for providing an image of a fluid downhole, comprising:
    illuminating the fluid downhole with light using a light source;
    using a pyroelectric detector to detect light from the fluid at least one wavelength and provide signals corresponding to the detected light; and
    using a processor to process the signals to provide a visual image of at least one of oil, gas and solid present in the fluid.

10. The method of claim 9, wherein the light is a broadband light.

11. The method of claim 10, wherein the at least one wavelength includes at least two wavelengths and wherein one such wavelength is one of: (i) a wavelength at which light is minimally absorbed by natural oil present in a downhole formation; (ii) a wavelength at which light is minimally absorbed by natural oil present in a formation and a wavelength at which light is highly absorbed by the natural oil present in the formation; (iii) a wavelength from about 1300 nm to about 1600 nm; and (iv) a wavelength at which light is minimally absorbed by a natural oil present in a formation and is highly absorbed by water present in the formation.

12. The method of claim 11, further comprising tuning the pyroelectric detector to the at least two wavelengths during withdrawing of the fluid from a formation downhole and processing the signals to provide the image in-situ.

13. The method of claim 9 further comprising passing the fluid through a chamber and continuously detecting the light over a selected period of time to provide in-situ optical images of the fluid over the selected time period.

14. A computer-readable medium accessible to a processor for executing instructions contained in a computer program embedded in the computer-readable medium, wherein the computer program comprises:
    instructions to activate a light source for illuminating a fluid;
    instructions to tune a pyroelectric detector that is positioned to detect light from the fluid at a plurality of wavelengths;
    instructions to receive signals from the pyroelectric detector; and
    instructions to process the received signals to provide a visual image of at least one of oil, gas, water and solid present in the fluid.

15. The computer-readable-medium of claim 14, wherein the computer program further comprises instructions to compare absorbance at the plurality of wavelengths to provide the visual image of the fluid.

16. A system for providing images of a fluid extracted from a formation, comprising:
    a tool deployable into a wellbore by a conveying member from a surface location, wherein the tool includes:
    a pump for extracting the fluid from the formation;
    a chamber for receiving the extracted fluid and allowing the received fluid to pass therethrough;
    a light source that illuminates the fluid in the chamber;
    a pyroelectric detector that detects light from fluid at a plurality of wavelengths and produces signals corresponding to the detected light; and
    a processor that utilizes information relating to the signals produced by the detector to provide an optical image of at least one of oil, gas, water and solid present in the fluid.

17. The system of claim 16, wherein the processor compares absorbance at least two wavelengths to provide the optical image of the fluid.

18. The system of claim 17, wherein the processor assigns a different color to each of oil, water, gas and solids in the optical image.

* * * * *